United States Patent
Zhou et al.

(10) Patent No.: US 10,421,837 B2
(45) Date of Patent: *Sep. 24, 2019

(54) POLYMERIC AMINE SYNERGIST COMPOSITIONS

(71) Applicant: Hewlett-Packard Development Company, L.P., Fort Collins, CO (US)

(72) Inventors: Zhang-Lin Zhou, San Diego, CA (US); Rodney David Stramel, San Diego, CA (US); Gregg A. Lane, San Diego, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 21 days.

This patent is subject to a terminal disclaimer.

(21) Appl. No.: 15/562,096

(22) PCT Filed: Dec. 15, 2015

(86) PCT No.: PCT/US2015/065771

§ 371 (c)(1),
(2) Date: Sep. 27, 2017

(87) PCT Pub. No.: WO2017/007505

PCT Pub. Date: Jan. 12, 2017

(65) Prior Publication Data

US 2018/0072845 A1  Mar. 15, 2018

Related U.S. Application Data

(63) Continuation of application No. PCT/US2015/039819, filed on Jul. 9, 2015.

(51) Int. Cl.

| | | |
|---|---|---|
| C09D 11/101 | (2014.01) | |
| C08G 65/333 | (2006.01) | |
| C08K 5/18 | (2006.01) | |
| C08G 65/331 | (2006.01) | |
| C08G 65/334 | (2006.01) | |
| C08G 65/335 | (2006.01) | |
| C07C 217/86 | (2006.01) | |
| C09D 11/102 | (2014.01) | |
| C09D 11/38 | (2014.01) | |
| C09D 11/54 | (2014.01) | |

(52) U.S. Cl.
CPC ...... *C08G 65/33396* (2013.01); *C07C 217/86* (2013.01); *C08G 65/3315* (2013.01); *C08G 65/3346* (2013.01); *C08G 65/3356* (2013.01); *C08G 65/33313* (2013.01); *C08K 5/18* (2013.01); *C09D 11/101* (2013.01); *C09D 11/102* (2013.01); *C09D 11/38* (2013.01); *C09D 11/54* (2013.01)

(58) Field of Classification Search
CPC ..... C09D 11/101; C09D 11/102; C09D 11/38; C09D 11/54; C08K 5/18; C08G 65/33396; C08G 65/3315; C08G 65/33313; C08G 65/3346; C08G 65/3356; C07C 217/86

See application file for complete search history.

(56) References Cited

U.S. PATENT DOCUMENTS

| | | | |
|---|---|---|---|
| 4,418,138 A | 11/1983 | Curtis | |
| 4,450,279 A | 5/1984 | Shirosaki et al. | |
| 4,459,416 A | 7/1984 | Curtis et al. | |
| 4,602,097 A | 7/1986 | Curtis | |
| 5,905,164 A | 5/1999 | Anderson et al. | |
| 5,907,046 A | 5/1999 | Bearson et al. | |
| 6,025,408 A | 2/2000 | Williams et al. | |
| 7,335,782 B2 | 2/2008 | Herlihy et al. | |
| 8,530,510 B2 * | 9/2013 | Loccufier | C07C 69/76 514/434 |
| 8,598,249 B2 | 12/2013 | Noirot et al. | |
| 8,946,449 B2 | 2/2015 | Madsen et al. | |
| 2004/0132862 A1 | 7/2004 | Woudenberg | |
| 2011/0195198 A1 | 8/2011 | Loccufier et al. | |
| 2013/0012611 A1 | 1/2013 | Davidson et al. | |
| 2014/0335326 A1 | 11/2014 | Gevaert et al. | |
| 2018/0112037 A1 * | 4/2018 | Zhou | C08K 5/18 |

FOREIGN PATENT DOCUMENTS

| | | |
|---|---|---|
| CN | 1594369 | 3/2005 |
| CN | 1594399 | 3/2005 |
| CN | 101665575 | 3/2010 |
| CN | 102250059 | 11/2011 |
| WO | 2002040464 | 5/2002 |
| WO | 2008061954 | 5/2008 |

(Continued)

OTHER PUBLICATIONS

International Search Report and Written Opinion dated Jun. 3, 2016 for PCT/US2015/065771; Applicant Hewlett-Packard Development Company L.P.

(Continued)

*Primary Examiner* — Sanza L. McClendon

(74) *Attorney, Agent, or Firm* — Thorpe North & Western LLP

(57) ABSTRACT

The present disclosure is drawn to polymeric amine synergist compositions. The polymeric amine synergist composition can include a polymeric amine synergist including an aminobenzene modified with a polyether chain connecting to the aminobenzene through an ether linkage. The polymeric amine synergist can be present in a reaction product mixture with either i) an aminophenol, or ii) a carbonate base.

15 Claims, 1 Drawing Sheet

(56) References Cited

FOREIGN PATENT DOCUMENTS

| WO | 2012003644 | 1/2012 |
| --- | --- | --- |
| WO | 2013146061 | 10/2013 |
| WO | 2013146062 | 10/2013 |
| WO | 2015010729 | 1/2015 |

OTHER PUBLICATIONS

Akat et al., Poly(ethylene glycol)-Thioxanthone Prepared by Diels-Alder Click Chemistry as One-Component Polymeric Photoinitiator for Aqueous Free-Radical Polymerization, Journal of Polymer Science: Part A, Polymer Chemistry DOI 10.1002/POLA 2010, pp. 2109-2114.

Cesur et al., Difunctional monomeric and polymeric photoinitiators: Synthesis and photoinitiating behaviors, Progress in Organic Coatings 86, 2015, pp. 71-78.

Gilman et al., Orientation in the 10-Thiaxanthenone Nucleus, Contribution from the Chemical Laboratory of Iowa State College, vol. 24, 1959, pp. 1914-1916.

Hammick et al., A New Synthesis of 1-Amino-4-methylthioxanthone and of Miracil D., Journal of the Chemical Society (Resumed), Issue 0, 1952, pp. 1077-1080.

Nazir et al., Donor-Acceptor Type Thioxanthones: Synthesis, Optical Properties, and Two-Photon Induced Polymerization, Macromolecules, American Chemical Society, ACS Publications, 2015, 7 pages.

Sharp, A New Synthesis of Lucanthone (Miracil D, Nilodin), Journal of the Chemical Society (Resumed), Issue 0, 1951, pp. 2961-2963.

Wen et al., Amphipathic hyperbranched polymeric thioxanthone photoinitiators (AHPTXs): Synthesis, characterization and photoinitiated polymerization, Polymer 50, 2009, pp. 3917-3923.

Yin-Zhi et al., Synthesis and Crystal Structure of 2-hydroxyl-4-methyl-thioxanthone, Frontiers of Materials, Chemical and Metallurgical Technologies, Advanced Materials Research, vols. 581-582, 2012, pp. 189-192.

* cited by examiner

100 ↘

> Reacting an aminophenol, a polyether modified with a leaving group, and a carbonate base in a single reaction step to yield a polymeric amine synergist that is an aminobenzene modified with a polyether chain connecting to the aminobenzene through an ether linkage — 110

> Preparing a polymeric amine synergist that is an aminobenzene modified with a polyether chain connecting to the aminobenzene through an ether linkage by reacting an aminophenol, a polyether modified with a leaving group, and a carbonate base in a single reaction step to yield a polymeric amine synergist that is an aminobenzene modified with a polyether chain connecting to the aminobenzene through an ether linkage — 210

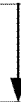

> Admixing the polymeric amine synergist; a photo reactive binder; a photo initiator; a colorant; and a liquid vehicle including co-solvent and water — 220

FIG. 2

POLYMERIC AMINE SYNERGIST COMPOSITIONS

BACKGROUND

The inkjet printing industry uses various types of inks, such as oil-based inks, solvent-based (non-aqueous) inks, water-based inks, and solid inks (which are melted in preparation for dispensing). Solvent-based inks are fast drying, and as a result, are widely used for industrial printing. When solvent-based inks containing binders and other ingredients are jetted onto a substrate, the solvent(s) partially or fully evaporate from the ink, leaving the binder and other ingredients such as pigment particles on the printed substrate in the form of a dry film. During the drying process, the solvents, which are often volatile organic compounds (VOC), emit vapors, and therefore can pollute the environment. The amount of pollution produced can increase greatly with higher printing speeds or for wide format images, where large amounts of ink are deposited onto a substrate.

As a result of this and other concerns, efforts related to preparing inks that are environmentally friendly have moved some research in the direction of water-based inks. However, radiation-curable (or photon-curable) water-based ink compositions are noticeably limited among available options due to their specific formulation properties. Accordingly, the development of radiation radiation-curable water-based ink compositions that exhibit, when printed, specific desirable printing properties, e.g., jetting properties as well as improved adhesion, would be an advancement in the field of inkjet technology.

BRIEF DESCRIPTION OF THE DRAWINGS

FIG. 1 is a diagram depicting a method of making a polymeric amine synergist in accordance with an example of the present disclosure; and FIG. 2 is a diagram depicting a method of making a photo curable ink in accordance with examples of the present disclosure.

DETAILED DESCRIPTION

The present disclosure is drawn to polymeric amine synergist compositions and methods of preparing polymeric amine synergists. In one example, the polymeric amine synergist compositions can include a polymeric amine synergist including an aminobenzene modified with a polyether chain connecting to the aminobenzene through an ether linkage. The polymeric amine synergist can be present in a reaction product mixture with either i) an aminophenol, or ii) a carbonate base. For example, the aminophenol and/or the carbonate base can remain in the composition in minor or even residual amounts after carrying out certain methods of the present disclosure.

The present disclosure also provides methods of making polymeric amine synergists including an aminobenzene modified with a polyether chain connecting to the aminobenzene through an ether linkage. The polymeric amine synergists can be water soluble and stable in aqueous inks, such as aqueous thermal inkjet inks, for example. The polymeric amine synergists also resist migration in the ink after curing. Thus, the polymeric amine synergists of the present disclosure overcome some of the drawbacks of other synergists and photo initiators which do not behave in this positive manner in aqueous systems. Some small molecular weight synergists, such as methyldiethanolamine, triethanolamine, and its analogs, can have unwanted odor, toxicity, and migration in cured materials. On the other hand, many polymeric synergists and photo initiators are not water soluble and are difficult to formulate into aqueous inks. Thus, in accordance with this, the present disclosure is drawn to improved methods of making polymeric amine synergists. The methods described herein include reaction pathways that are simple and provide high yields of the polymeric amine synergists. These methods can be adapted for large-scale synthesis of polymeric amine synergists.

Thus, in one example, and as shown in FIG. 1, a method of making a polymeric amine synergist 100 can include the step of reacting 110 an aminophenol, a polyether modified with a leaving group, and a carbonate base in a single reaction step to yield a polymeric amine synergist that is an aminobenzene modified with a polyether chain connecting to the aminobenzene through an ether linkage.

In another example, and as shown in FIG. 2, a method of making a photo curable ink 200 can include preparing 210 a polymeric amine synergist, and admixing 220 the polymeric amine synergist; a photo reactive binder; a photo initiator; a colorant; and a liquid vehicle including co-solvent and water together to form the ink. Specifically, the step of preparing the polymeric amine synergist can include reacting an aminophenol, a polyether modified with a leaving group, and a carbonate base in a single reaction step to yield a polymeric amine synergist that is an aminobenzene modified with a polyether chain connecting to the aminobenzene through an ether linkage.

In another example, a photo curable ink can include a polymeric amine synergist composition having a polymeric amine synergist including an aminobenzene modified with a polyether chain connecting to the aminobenzene through an ether linkage. The ink can further include an aminophenol, or a carbonate base, or combination thereof, e.g., as a residual component(s) remaining after carrying out a method of the present disclose. The ink can further include a photo reactive binder; a photo initiator; a colorant; and a liquid vehicle including co-solvent and water.

Accordingly, a polymeric amine synergist can include an aminobenzene modified with a polyether chain connecting to the aminobenzene through an amide linkage. As used herein, "aminobenzene" refers to the compound also referred to as aniline or phenylamine, as well as analogs of this compound with attached R-groups, such as dimethylaniline. The amino group of the aminobenzene can be a primary amine, secondary amine, or tertiary amine.

The polyether chain can be a polyglycol, paraformaldehyde, or other polyether. For example, the polyether chain can be polyethylene glycol (PEG), methoxypolyethylene glycol (MPEG), polypropylene glycol (PPG), polybutylene glycol (PBG), or a polyglycol copolymer. In one specific example, the polyether chain can be selected from polyethylene glycol, polypropylene glycol, and a copolymer of polyethylene glycol and polypropylene glycol. In another specific example, the polyether chain can be derived from a portion of a commercially available polyether amine such as Jeffamine® ED-900, Jeffamine® M-1000 (both available from Huntsman Corporation), or others. Various molecular weights of polyether can be suitable. The type of polyether chain and the molecular weight of the polyether chain can in some cases affect the solubility of the final polymeric amine synergist. For example, a higher ratio of oxygen atoms to carbon atoms in the polyether chain tends to make the polymeric amine synergist more soluble. The molecular weight of the polyether chain can also affect the degree to which the polymeric amine synergist can migrate in a cured ink. Longer polyether chains can make it more difficult for the polymeric amine synergist to move within a cured ink, thus decreasing migration. Therefore, the type of polyether chain can be selected to give good water solubility and low migration of the polymeric amine synergist in cured ink. In one example, the polyether chain can be a polyglycol having at least 5 glycol monomer units.

The polyether chain can connect to the aminobenzene through an ether linkage. As used herein, connecting to the aminobenzene through an ether linkage means that a single oxygen atom is bonded both to a carbon atom in the aromatic ring of the aminobenzene and to a carbon atom in the polyether chain. This ether linkage can be formed by a suitable reaction, such as a substitution reaction or a condensation reaction.

The aminobenzene, polyether chain, and ether linkage do not necessarily make up the entire polymeric amine synergist. For example, additional groups can be attached along the polyether chain or at the opposite end of the polyether chain. In some cases, one or more additional aminobenzene moieties can be attached to the polyether chain. These additional aminobenzene moieties can connect to the polyether chain through ether linkages. In one example, an additional aminobenzene moiety can connect to an opposite end of the polyether chain through an ether linkage. In other examples, the polyether chain can have multiple branches and each branch can terminate with an aminobenzene moiety connected to the polyether chain through an ether linkage. Specific examples of such polymeric amine synergists are described in detail below.

In some examples, the aminobenzene with the ether linkage can have a general formula according to Formula 1:

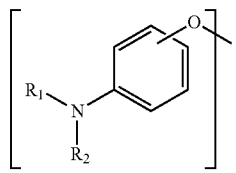

(1)

In Formula 1, the ether linkage is illustrated as an oxygen atom bonded to the aromatic ring of the aminobenzene. The ether linkage can be bonded to any of the available carbon atoms in the ring by replacing a hydrogen atom. The groups $R_1$ and $R_2$ can be independently a hydrogen atom, an unsubstituted alkyl, a substituted alkyl, an unsubstituted alkenyl, a substituted alkenyl, an unsubstituted aryl, a substituted aryl, an unsubstituted aralkyl, a substituted aralkyl, a halogen atom, $-NO_2$, $-O-R_d$, $-CO-R_d$, $-CO-O-R_d$, $-O-CO-R_d$, $-CO-NR_dR_e$, $-NR_dR_e$, $-NR_d-CO-R_e$, $-NR_d-CO-O-R_e$, $-NR_d-CO-NR_eR_f$, $-SR_d$, $-SO-R_d$, $-SO_2-R_d$, $-SO_2-O-R_d$, $-SO_2NR_dR_e$, or a perfluoroalkyl group, wherein $R_d$, $R_e$, and $R_f$ are independently a hydrogen atom, an unsubstituted alkyl, a substituted alkyl, an unsubstituted alkenyl, a substituted alkenyl, an unsubstituted aryl, a substituted aryl, an unsubstituted aralkyl, or a substituted aralkyl. In one specific example, $R_1$ and $R_2$ can each be a hydrogen atom. Formula 1 illustrates only the aminobenzene with the ether linkage. A complete polymeric amine synergist can be formed by combining an aminobenzene and ether linkage as in Formula 1 with a polyether chain. The polyether chain can be bonded to the oxygen atom of the ether linkage In some examples, the polymeric amine synergist can have a general formula according to one of Formulas 2-5:

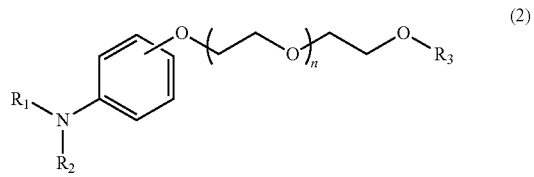

(2)

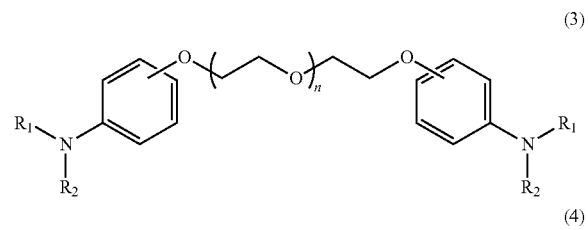

(3)

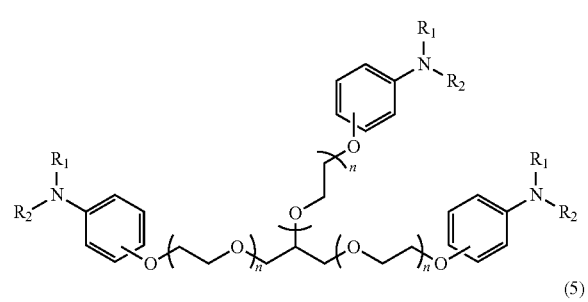

(4)

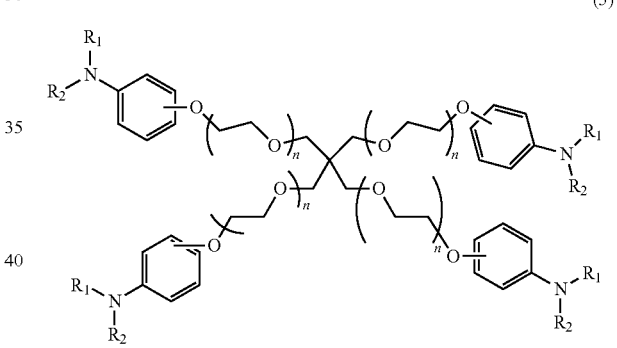

(5)

In each of Formulas 2-5, the groups $R_1$, $R_2$, and $R_3$ can independently be a hydrogen atom, an unsubstituted alkyl, a substituted alkyl, an unsubstituted alkenyl, a substituted alkenyl, an unsubstituted aryl, a substituted aryl, an unsubstituted aralkyl, a substituted aralkyl, a halogen atom, $-NO_2$, $-O-R_d$, $-CO-R_d$, $-CO-O-R_d$, $-O-CO-R_d$, $-CO-NR_dR_e$, $-NR_dR_e$, $-NR_d-CO-R_e$, $-NR_d-CO-O-R_e$, $-NR_d-CO-NR_eR_f$, $-SR_d$, $-SO-R_d$, $-SO_2-R_d$, $-SO_2-O-R_d$, $-SO_2NR_dR_e$, or a perfluoroalkyl group. In these examples, $R_d$, $R_e$, and $R_f$ can independently be a hydrogen atom, an unsubstituted alkyl, a substituted alkyl, an unsubstituted alkenyl, a substituted alkenyl, an unsubstituted aryl, a substituted aryl, an unsubstituted aralkyl, or a substituted aralkyl. In one specific example, $R_1$ to $R_3$ can each be a hydrogen atom. The number of monomer units n can be any integer from 5 to 200.

As shown in Formulas 2-5, the polymeric amine synergist can include 1, 2, 3, or 4 aminobenzene moieties connected to a branching polyether chain. In other examples, the polyether chain can have more than 4 branches terminating in aminobenzene moieties.

In one example, the polymeric amine synergist can have a general formula according to Formula 6:

(6)

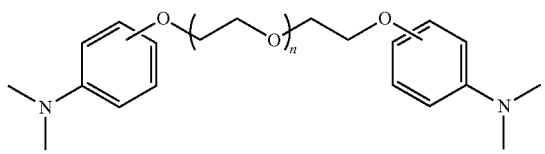

In the specific example described by Formula 6, n can be any integer, e.g., 5 to 200.

The molecular weight of the polymeric amine synergist can affect its degree of migration in cured ink. For clarity, unless otherwise noted, molecular weights for polymers are weight average molecular weights (Mw). In accordance with this, a polymeric amine synergist with a weight average molecular weight (Mw) of about 500 Mw or more can have reduced migration in cured ink compared with a small molecule photo initiator or sensitizer. Migration can be further reduced by increasing the molecular weight of the polymeric amine synergist to about 1000 Mw or more. In one example, the polymeric amine synergist can have a molecular weight from about 500 Mw to about 5000 Mw. Polyethers of various molecular weights are available, allowing for the production of polymeric amine synergists with various weight average molecular weights. In some examples, the polyether chain can be selected from PEG 550, PEG 600, and PEG 1000. In polymeric amine synergists having multiple aminobenzene moieties, a smaller molecular weight polyether chain can be used while still maintaining a high overall molecular weight of the polymeric amine synergists. The molecular weight of the polymeric amine synergist can also be changed by adding R groups to the aminobenzene. It is noted that when referring to "R groups" generically herein, this term is defined to include at least H and organic side chain side groups and other specific constituents described and defined elsewhere herein, e.g., R, $R_1$, $R_2$, $R_3$, $R_d$, $R_e$, $R_f$, etc.

The molecular weight (Mw) of the polymeric amine synergist can also affect its solubility in water. In some cases, the polyether chain can be a water soluble polyether. Although the aminobenzene alone can be insoluble in water, adding the soluble polyether chain can make the entire polymeric amine synergist soluble. In such cases, the soluble polyether can have a sufficient molecular weight so that its solubility properties overcome the insolubility of the aminobenzene. In other cases, water soluble R groups can be added to the aminobenzene to increase the solubility of the polymeric amine synergist. In one example, the polymeric amine synergist can have a water solubility of at least 0.5 wt %.

Typical aqueous ink jet inks can have a pH in the range of 7 to 12. Some commercially available photo initiators and synergists with ester linkages can break down in such basic conditions. The ether linkage in the polymeric amine synergists according to the present disclosure can be stable under these conditions. In some examples, the polymeric amine synergist can be stable in water up to a pH from 7 to 12. In other examples, the polymeric amine synergist can be stable in water up to a pH of 8 or higher. As used herein, "stable" refers to the ability of the polymeric amine synergist to have a shelf life of at least 1 year. Typically, aqueous ink jet inks can have a shelf life of greater than 1 year, greater than 2 years, or longer.

The polymeric amine synergist described above can be formed using a multi-step process involving a reaction with sodium hydroxide. A reaction pathway for one example of this process is shown in Formula 7:

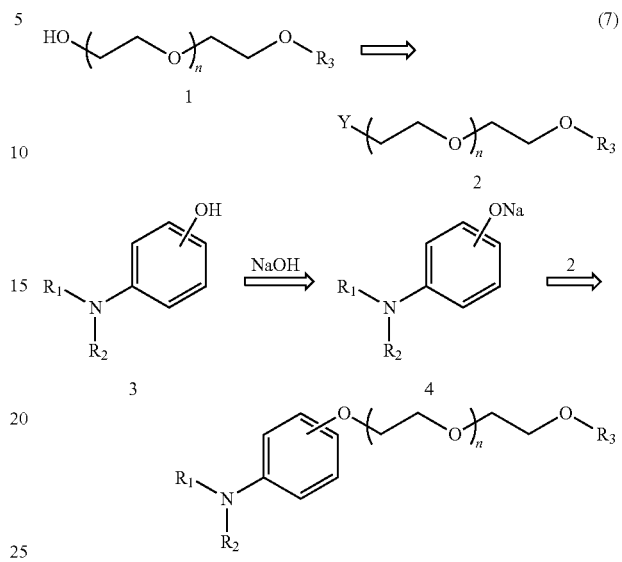

In the pathway shown in Formula 7, $R_1$ to $R_3$ each independently represent a hydrogen atom, a substituted or unsubstituted alkyl, alkenyl, aryl or aralkyl group or a group selected from a halogen atom, $—NO_2$, $—O—R_d$, $—CO—O—R_d$, $—O—CO—R_d$, $—CO—NR_dR_e$, $—NR_dR_e$, $—NR_d—CO—R_e$, $—NR_d—CO—O—R_e$, $—NR_d—CO—NR_eR_f$, $—SR_d$, $—SO—R_d$, $—SO_2—R_d$, $—SO_2—O—R_d$, $—SO_2NR_dR_e$ or a perfluoroalkyl group. $R_d$, $R_e$ and $R_f$ independently represent a hydrogen or a substituted or unsubstituted alkyl, alkenyl, aryl or aralkyl group. The number of monomer units n can be any integer from 5 to 200. The group Y can be a leaving group such as —Cl, —Br, —I, —OTs, or —OTf.

As shown in Formula 7, a monosubstituted polyethylene glycol ether (1) is reacted with a leaving group to form a leaving group modified polyethylene glycol (2). Various reagents can be used to add the leaving group. For example, a halogenation reagent can be used to add —Cl, —Br, or —I leaving groups; a tosylation reagent can be used to add a —OTs leaving group; and a triflating reagent can be used to add a —OTf leaving group. An aminophenol (3) is reacted with NaOH to form a corresponding sodium salt (4). The sodium salt is then reacted with the leaving group modified polyethylene glycol (2) to form the polymeric amine synergist. Lines leading to the center of aromatic rings in the aminophenol (3), the sodium salt (4), and the final polymeric amine synergist signify that the group can be attached at any available location on the ring.

The reaction pathway shown in Formula 7 is complex and can result in low yields, due to the steps of reacting the aminobenzene with NaOH to form the sodium salt, followed by reacting the sodium salt with the leaving group modified polyethylene glycol. This pathway typically results in yields ranging from 10% to 50%. The leaving group modified polyethylene glycol cannot be reacted with the aminobenzene and the NaOH simultaneously, because the hydroxyl (OH⁻) produced from the NaOH would replace the leaving group on the leaving group modified polyethylene glycol. The polyethylene glycol would then not be able to connect to the aminobenzene. For this reason, NaOH is reacted with the aminobenzene first to form a sodium salt of the aminobenzene, and then in a separate step the sodium salt is reacted with the leaving group modified polyethylene glycol to form the final polymeric amine synergist.

To reduce the complexity of the synthesis process and increase the yield of polymeric amine synergist, a different reaction pathway can involve reacting the aminobenzene directly with the leaving group modified polyethylene glycol in a single step. An example of such a pathway is shown in Formula 8:

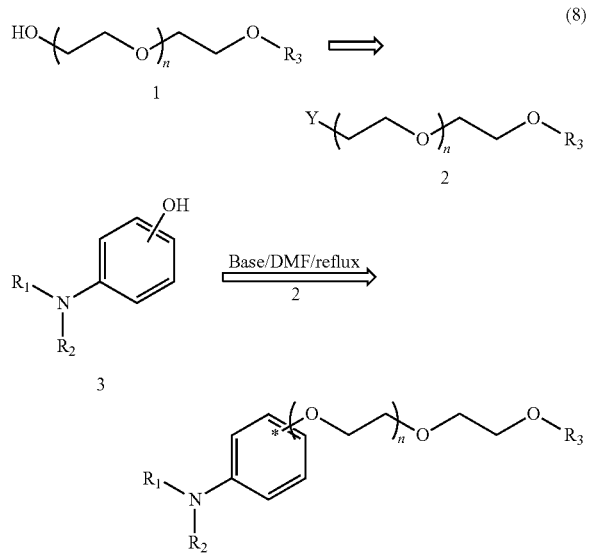

In the pathway shown in Formula 8, $R_1$ to $R_3$ each independently represent a hydrogen atom, a substituted or unsubstituted alkyl, alkenyl, aryl or aralkyl group or a group selected from a halogen atom, $-NO_2$, $-O-R_d$, $-CO-R_d$, $-CO-O-R_d$, $-O-CO-R_d$, $-CO-NR_dR_e$, $-NR_dR_e$, $-NR_d-CO-R_e$, $-NR_d-CO-O-R_e$, $-NR_d-CO-NR_eR_f$, $-SR_d$, $-SO-R_d$, $-SO_2-R_d$, $-SO_2-O-R_d$, $-SO_2NR_dR_e$ or a perfluoroalkyl group. $R_d$, $R_e$ and $R_f$ independently represent a hydrogen or a substituted or unsubstituted alkyl, alkenyl, aryl or aralkyl group. The number of monomer units n can be any integer from 5 to 200. The group Y can be a leaving group such as $-Cl$, $-Br$, $-I$, $-OTs$, or $-OTf$.

According to this pathway, a monosubstituted polyethylene glycol ether (1) is reacted with a leaving group to form a leaving group modified polyethylene glycol (2). Then, an aminophenol (3) is reacted directly with the leaving group modified polyethylene glycol (2) in the presence of a base and dimethylformamide (DMF) at reflux conditions. The base used in this reaction is a base other than NaOH, which does not replace the leaving group of the leaving group modified polyethylene glycol (2). Without being bound to a particular mechanism, it is believed that the base can be a base that does not produce a hydroxyl group that would replace the leaving group on the leaving group modified polyethylene glycol (2). In certain examples, the base can be a carbonate base, such as sodium carbonate ($Na_2CO_3$), potassium carbonate ($K_2CO_3$) or cesium carbonate ($Cs_2CO_3$). In this reaction, the aminophenol (3) becomes bonded directly to the polyethylene glycol through an ether linkage.

Thus, the step of reacting the aminophenol with NaOH to form a sodium salt can be eliminated, simplifying the process for synthesizing the polymeric amine synergist. This pathway can also provide a higher yield. In some examples, the yield of the polymeric amine synergist can be from 75% to 95%.

In more general terms, a method of making a polymeric amine synergist in accordance with the present disclosure can include: reacting an aminophenol, a polyether modified with a leaving group, and a carbonate base in a single reaction step to yield a polymeric amine synergist that is an aminobenzene modified with a polyether chain connecting to the aminobenzene through an ether linkage. The polymeric amine synergist can have any of the structures described above.

In some examples, the aminophenol can have a general formula according to Formula 9:

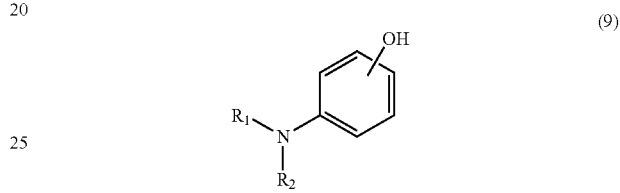

In Formula 9, the $-OH$ group can be bonded to any of the available carbon atoms in the aromatic ring by replacing a hydrogen atom. The groups $R_1$ and $R_2$ can be independently selected from: a hydrogen atom, an unsubstituted alkyl, a substituted alkyl, an unsubstituted alkenyl, a substituted alkenyl, an unsubstituted aryl, a substituted aryl, an unsubstituted aralkyl, a substituted aralkyl, a halogen atom, $-NO_2$, $-O-R_d$, $-CO-R_d$, $-CO-O-R_d$, $-O-CO-R_d$, $-CO-NR_dR_e$, $-NR_dR_e$, $-NR_d-CO-R_e$, $-NR_d-CO-O-R_e$, $-NR_d-CO-NR_eR_f$, $-SR_d$, $-SO-R_d$, $-SO_2-R_d$, $-SO_2-O-R_d$, $-SO_2NR_dR_e$, and a perfluoroalkyl group, wherein $R_d$, $R_e$, and $R_f$ are independently selected from: a hydrogen atom, an unsubstituted alkyl, a substituted alkyl, an unsubstituted alkenyl, a substituted alkenyl, an unsubstituted aryl, a substituted aryl, an unsubstituted aralkyl, and a substituted aralkyl. In one specific example, $R_1$ and $R_2$ can each be a hydrogen atom. In other examples, the aminophenol can be an alkyl aminophenol or a dialkylaminophenol.

In some examples, the carbonate base used in the method can be sodium carbonate, potassium carbonate, cesium carbonate, sodium bicarbonate, potassium bicarbonate, cesium bicarbonate, or a combination thereof. In one specific example, the carbonate base can include sodium carbonate or a mixture of sodium carbonate and another base.

The carbonate base can generally be added to the reaction in an amount that is effective for bonding the aminophenol to the leaving group modified polyether. In some examples, the amount of carbonate base used can be 1 equivalent or more of the carbonate base, relative to the amount of the aminophenol present in the reaction. In further examples, the amount of carbonate base can be from about 1 equivalent to about 2 equivalents, relative to the amount of the aminophenol. In a specific example, the amount of carbonate base can be from about 1.1 equivalents to about 1.2 equivalents, relative to the amount of the aminophenol.

Although the reaction pathway shown in Formula 8 uses DMF as a solvent in the reaction between the aminophenol and the polyether modified with a leaving group, other solvents can also be used. Suitable solvents for this reaction can include DMF, THF, ethyl acetate, toluene, xylene, and mixtures thereof.

The polyether modified with a leaving group used in the reaction can be formed by reacting a leaving group with a polyether chain. In some examples, the polyether chain can include polyethylene glycol, polypropylene glycol, or a copolymer of polyethylene glycol and polypropylene glycol. In further examples, the polyether chain can be PEG 550, PEG 600, or PEG 1000.

In additional examples, the polyether modified with the leaving group can have a general formula according to one of Formulas 10-13:

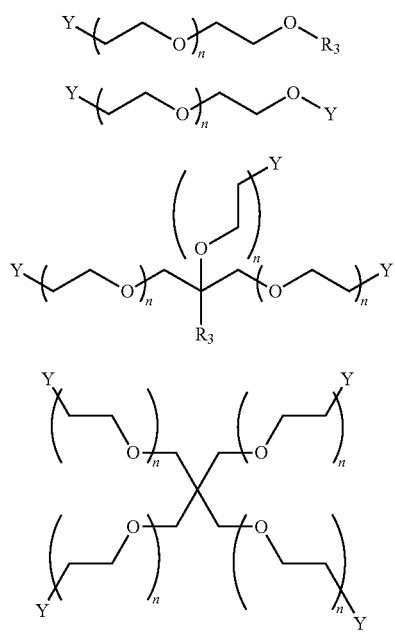

In each of Formulas 10-13, the group $R_3$ can be a hydrogen atom, an unsubstituted alkyl, a substituted alkyl, an unsubstituted alkenyl, a substituted alkenyl, an unsubstituted aryl, a substituted aryl, an unsubstituted aralkyl, a substituted aralkyl, a halogen atom, —$NO_2$, —O—$R_d$, —CO—$R_d$, —CO—O—$R_d$, —CO—$NR_dR_e$, —$NR_dR_e$, —$NR_d$—CO—$R_e$, —$NR_d$—CO—O—$R_e$, —$NR_d$—CO—$NR_eR_f$, —$SR_d$, —SO—$R_d$, —$SO_2$—$R_d$, —$SO_2$—O—$R_d$, —$SO_2NR_dR_e$, or a perfluoroalkyl group. In these examples, $R_d$, $R_e$, and $R_f$ can independently be a hydrogen atom, an unsubstituted alkyl, a substituted alkyl, an unsubstituted alkenyl, a substituted alkenyl, an unsubstituted aryl, a substituted aryl, an unsubstituted aralkyl, or a substituted aralkyl. In one specific example, $R_3$ can be a hydrogen atom. The number of monomer units n can be any integer from 5 to 200. The group Y can be chloride, bromide, iodide, tosylate, or triflate.

Another example of a general pathway for forming a polymeric amine synergist in accordance with the present disclosure is shown in Formula 14:

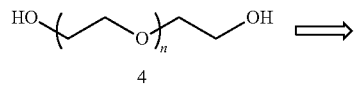

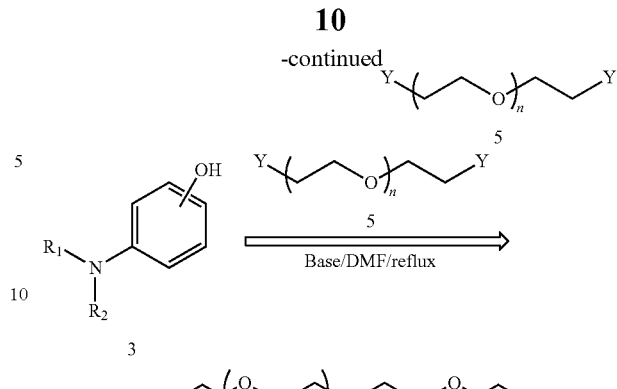

In the pathway shown in Formula 14, $R_1$ and $R_2$ each independently represent a hydrogen atom, a substituted or unsubstituted alkyl, alkenyl, aryl or aralkyl group or a group selected from a halogen atom, —$NO_2$, —O—$R_d$, —CO—$R_d$, —CO—O—$R_d$, —O—CO—$R_d$, —CO—$NR_dR_e$, —$NR_dR_e$, —$NR_d$—CO—$R_e$, —$NR_d$—CO—O—$R_e$, —$NR_d$—CO—$NR_eR_f$, —$SR_d$, —SO—$R_d$, —$SO_2$—$R_d$, —$SO_2$—O—$R_d$, —$SO_2NR_dR_e$ or a perfluoroalkyl group. $R_d$, $R_e$ and $R_f$ independently represent a hydrogen or a substituted or unsubstituted alkyl, alkenyl, aryl or aralkyl group. The number of monomer units n can be any integer from 5 to 200. The group Y can be a leaving group such as —Cl, —Br, —I, —OTs, or —OTf.

According to this pathway, polyethylene glycol (4) is reacted with a leaving group reagent to form a leaving group modified polyethylene glycol (5). An aminophenol (3) is reacted with the leaving group modified polyethylene glycol and a carbonate base to form the polymeric amine synergist. Lines leading to the center of aromatic rings in the aminophenol (3) and the final polymeric amine synergist signify that the group can be attached at any available location on the ring.

A further example of a general pathway for forming a polymeric amine synergist keeping with the present disclosure is shown in Formula 15:

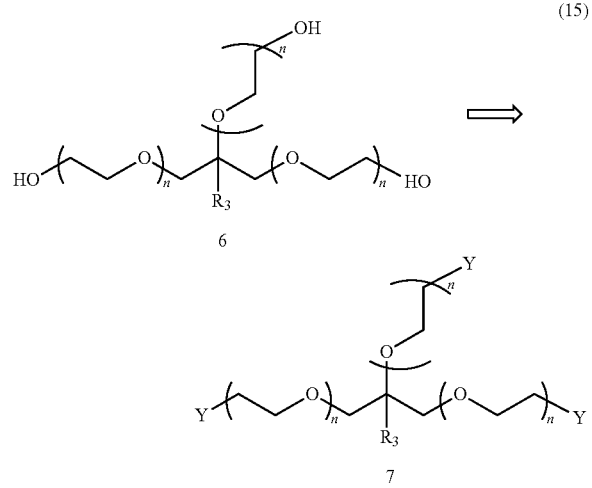

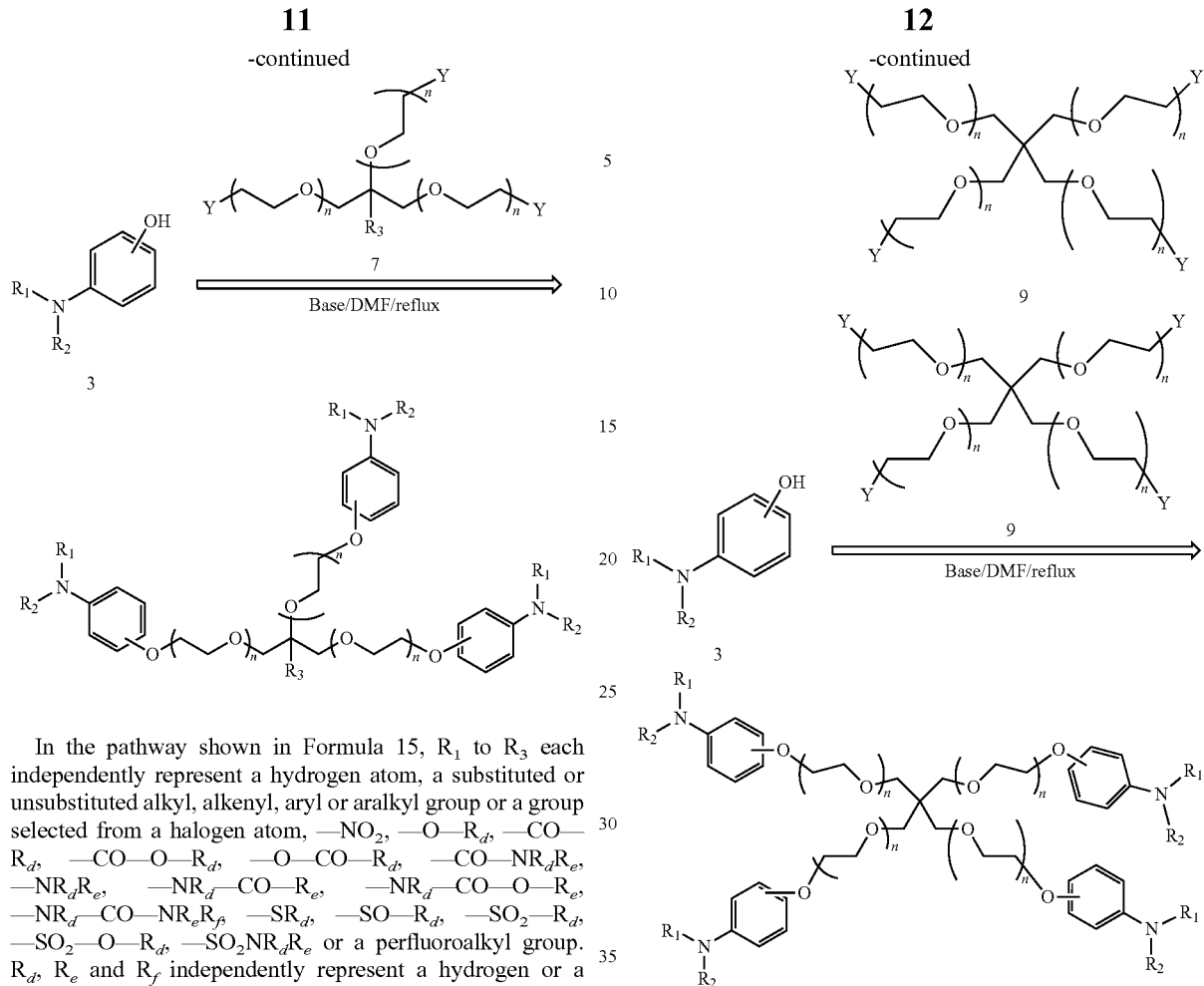

In the pathway shown in Formula 15, $R_1$ to $R_3$ each independently represent a hydrogen atom, a substituted or unsubstituted alkyl, alkenyl, aryl or aralkyl group or a group selected from a halogen atom, $-NO_2$, $-O-R_d$, $-CO-R_d$, $-CO-O-R_d$, $-O-CO-R_d$, $-CO-NR_dR_e$, $-NR_dR_e$, $-NR_d-CO-R_e$, $-NR_d-CO-O-R_e$, $-NR_d-CO-NR_eR_f$, $-SR_d$, $-SO-R_d$, $-SO_2-R_d$, $-SO_2-O-R_d$, $-SO_2NR_dR_e$ or a perfluoroalkyl group. $R_d$, $R_e$ and $R_f$ independently represent a hydrogen or a substituted or unsubstituted alkyl, alkenyl, aryl or aralkyl group. The number of monomer units n can be any integer from 5 to 200. The group Y can be a leaving group such as $-Cl$, $-Br$, $-I$, $-OTs$, or $-OTf$.

According to this pathway, a glycerol polyethylene glycol derivative (6) is reacted with a leaving group reagent to form a leaving group modified glycerol polyethylene glycol derivative (7). An aminophenol (3) is reacted with the leaving group modified glycerol polyethylene glycol derivative and a carbonate base to form the polymeric amine synergist. Lines leading to the center of aromatic rings in the aminophenol (3) and the final polymeric amine synergist signify that the group can be attached at any available location on the ring.

Yet another example of a general pathway for forming a polymeric amine synergist in accordance with the present disclosure is shown in Formula 16:

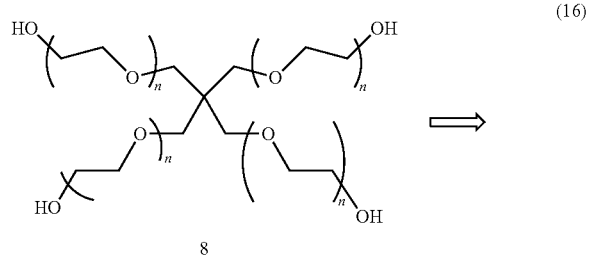

(16)

In the pathway shown in Formula 16, $R_1$ and $R_2$ each independently represent a hydrogen atom, a substituted or unsubstituted alkyl, alkenyl, aryl or aralkyl group or a group selected from a halogen atom, $-NO_2$, $-O-R_d$, $-CO-R_d$, $-CO-O-R_d$, $-O-CO-R_d$, $-CO-NR_dR_e$, $-NR_dR_e$, $-NR_d-CO-R_e$, $-NR_d-CO-O-R_e$, $-NR_d-CO-NR_eR_f$, $-SR_d$, $-SO-R_d$, $-SO_2-R_d$, $-SO_2-O-R_d$, $-SO_2NR_dR_e$ or a perfluoroalkyl group. $R_d$, $R_e$ and $R_f$ independently represent a hydrogen or a substituted or unsubstituted alkyl, alkenyl, aryl or aralkyl group. The number of monomer units n can be any integer from 5 to 200. The group Y can be a leaving group such as $-Cl$, $-Br$, $-I$, $-OTs$, or $-OTf$.

According to this pathway, a pentaerythritol polyethylene glycol derivative (8) is reacted with a leaving group to form a leaving group modified pentaerythritol polyethylene glycol derivative (9). An aminophenol (3) is reacted with the leaving group modified pentaerythritol polyethylene glycol derivative and a carbonate base to form the polymeric amine synergist. Lines leading to the center of aromatic rings in the aminophenol (3) and the final polymeric amine synergist signify that the group can be attached at any available location on the ring.

Formula 17 illustrates a detailed synthetic pathway for one example of a polymeric amine synergist in accordance with the present disclosure:

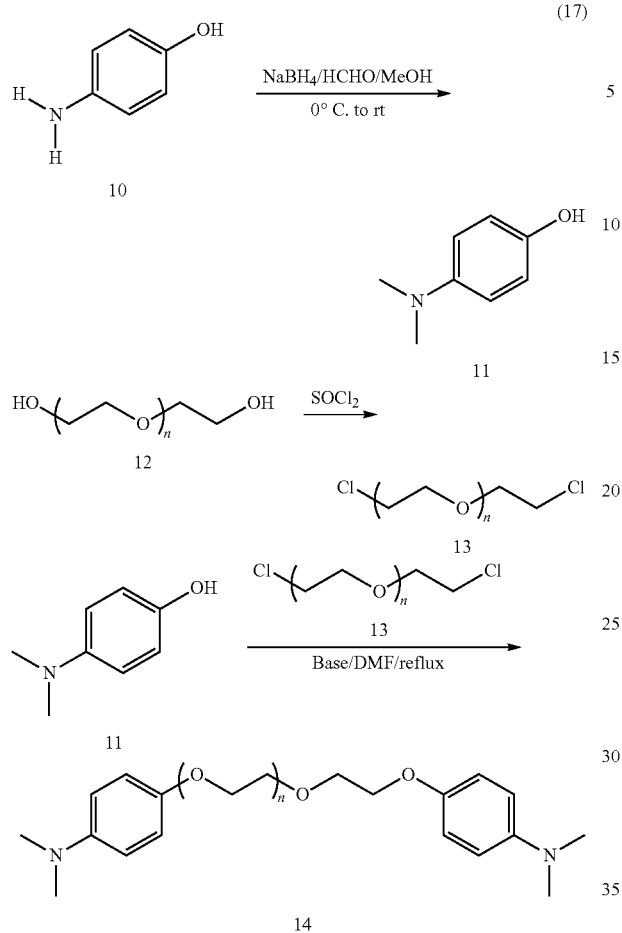

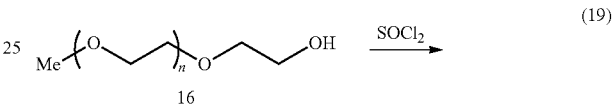

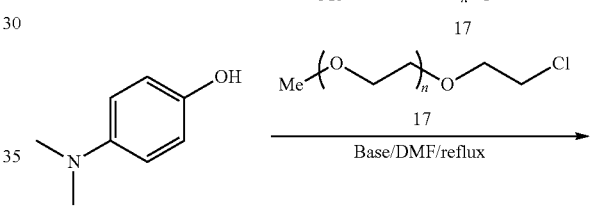

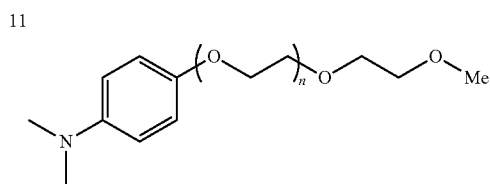

According to this pathway, 4-aminophenol (10) is reacted with sodium borohydride and formaldehyde in methanol to yield 4-dimethylaminophenol (11). Polyethylene glycol (12) is reacted with thionyl chloride in the presence of DMF to give dichloro polyethylene glycol (13). Finally, reaction of the 4-dimethylaminophenol (11) with the dichloro polyethylene glycol (13) in DMF under reflux in the presence of a carbonate base gives the desired polymeric amine synergist (14) in high yield.

An alternative pathway for synthesizing the same polymeric amine synergist is shown in Formula 18:

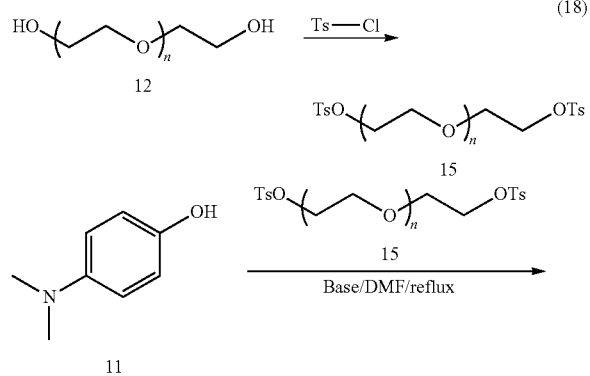

In this pathway, polyethylene glycol (12) is reacted with toluenesulfonyl chloride in the presence of pyridine to give polyethylene glycol di-tosylate (15). Then, 4-dimethylaminophenol (11) is reacted with the polyethylene glycol di-tosylate (15) in DMF under reflux in the presence of a carbonate base to give the desired polymeric amine synergist (14) in high yield.

A detailed synthetic pathway for forming another example of a polymeric amine synergist in accordance with the present disclosure is shown in Formula 19:

In this pathway, mono-methyl polyethylene glycol ether (16) is reacted with thionyl chloride in the presence of DMF to give chloro mono-methyl polyethylene glycol ether (17). Then, 4-dimethylaminophenol (11) is reacted with the chloro mono-methyl polyethylene glycol ether (17) in DMF under reflux in the presence of a carbonate base to give the desired polymeric amine synergist (18) in high yield.

Formula 20 illustrates an alternate pathway for forming the same polymeric amine synergist:

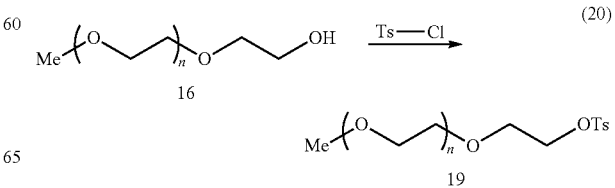

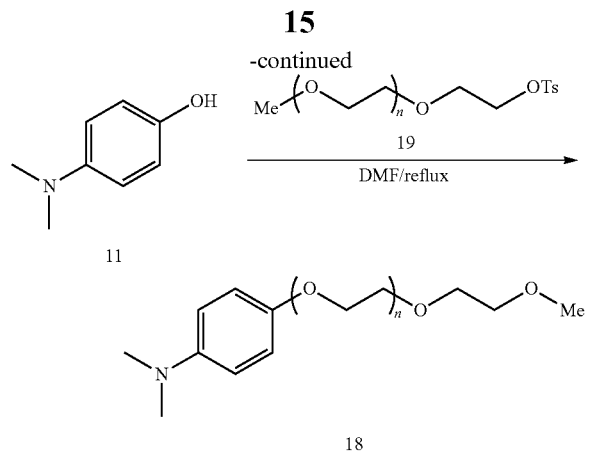

According to this pathway, mono-methyl polyethylene glycol ether (16) is reacted with p-toluenesulfonyl chloride in the presence of pyridine to give mono-methyl polyethylene glycol tosylate (19). Then, 4-dimethylaminophenol (11) is reacted with the mono-methyl polyethylene glycol tosylate (19) in DMF under reflux in the presence of a carbonate base to give the desired polymeric amine synergist (18) in high yield.

As mentioned, the present disclosure also extends to reaction product mixtures made using the reaction pathways described above. Generally, a reaction product mixture prepared by performing the reaction described above can include a polymeric amine synergist set forth herein. The reaction product mixture can also include excess reactants, such as an aminophenol, a polyether modified with a leaving group, a carbonate base, or a combination thereof. In some examples, the reaction product mixture can include a polymeric amine synergist that is an aminobenzene modified with a polyether chain connected to the aminobenzene through an ether linkage, and either an aminophenol, or a carbonate base. In examples including the aminophenol, the aminophenol can be the same compound used as a reactant to form the polymeric amine synergist.

In further examples, the reaction product mixture can include a carbonate base. In some cases, the carbonate base can be sodium carbonate, potassium carbonate, cesium carbonate, sodium bicarbonate, potassium bicarbonate, cesium bicarbonate, or a combination thereof. The amount of carbonate base in the reaction product mixture can depend on the amount of carbonate base added at the beginning of the reaction and the amount that is consumed during the reaction. In some cases, one mole of a carbonate base can react with one mole of the aminophenol during the reaction to form the polymeric amine synergist. Thus, one mole of the carbonate base is equal to 1 equivalent for a single mole of aminophenol. In some examples, the amount of carbonate base used in the reaction can be 1 equivalent or more of the carbonate base, relative to the amount of the aminophenol present in the reaction. In further examples, the amount of carbonate base can be from about 1 equivalent to about 2 equivalents, relative to the amount of the aminophenol. In a specific example, the amount of carbonate base can be from about 1 equivalent to about 1.2 equivalents or from about 1.1 equivalents to about 1.2 equivalents, relative to the amount of the aminophenol. In examples where all the aminophenol reacts to form the polymeric amine synergist, the amount of carbonate base left in the reaction product mixture can be, for example, up to about 1 equivalent, from about 0.1 equivalent to about 1 equivalent, up to about 0.2 equivalent, or from about 0.1 equivalent to about 0.2 equivalent, with respect to the amount of aminophenol used in the reaction.

The present disclosure also extends to photo curable inks. In some examples, a UV curable ink or an LED curable ink can be used, e.g., UV and/or LED curable ink. These inks can include a photo reactive binder, e.g., UV and/or LED, a photo initiator, a polymeric amine synergist, a colorant, and a liquid vehicle including a co-solvent and water. The polymeric amine synergist can be an aminobenzene modified with a polyether chain connecting to the aminobenzene through an ether linkage.

In some cases, the photo reactive binder can include a UV curable polyurethane and hydrophobic radiation-curable monomers. In one example, the photo reactive binder can include a water dispersible (meth)acrylated polyurethane, such as NeoRad® R-441 by NeoResins (Avecia). Other examples of photo (UV) reactive binders can include Ucecoat® 7710, Ucecoat® 7655 (available from Cytec), Neorad® R-440, Neorad® R-441, Neorad® R-447, Neorad® R-448 (available from DSM NeoResins), Bayhydrol® UV 2317, Bayhydrol® UV VP LS 2348 (available from Bayer), Lux 430, Lux 399, Lux 484 (available from Alberdingk Boley), Laromer® LR 8949, Laromer® LR 8983, Laromer® PE 22WN, Laromer® PE 55WN, Laromer® UA 9060 (available from BASF), or combinations thereof.

In general, ultraviolet (UV) curable ink can be cured after printing by application of UV radiation or light. Typically, UV curable inks include monomers that form polymers by free radical polymerization. The growing end of each polymer chain is a radical that reacts with additional monomers, transferring the radical to the end of the chain as each monomer is added. A photo initiator is used to form the first radicals to begin the polymerization process. The photo initiator is capable of absorbing UV light to generate radicals to react with the monomers. Two types of photo initiators can be used in UV curable compositions. Type I photo initiators are unimolecular photo initiators that undergo a hemolytic bond cleavage upon absorption of UV light, forming radicals. Type II photo initiators are bimolecular photo initiators. These are used as a system of a photo initiator with a synergist, which can together form radicals upon exposure to UV light. Some type II photo initiators react by hydrogen abstraction from the synergist to the photo initiator.

The polymeric amine synergists of the present disclosure can be used with type II photo initiators. The photo curable ink can include a type II photo initiator so that the photo initiator and amine synergist together can generate radicals during photo curing, e.g., UV curing or LED curing or UV LED curing. The type II photo initiators can act as the primary photo initiator in the photo curable ink, or they can act as a sensitizer for another co-photo initiator. Therefore, the photo curable ink can in some cases include a second photo initiator. Examples of radical co-photo initiators include, by way of illustration and not limitation, 1-hydroxy-cyclohexylphenylketone, benzophenone, 2,4,6-trimethyl-benzo-phenone, 4-methylbenzophenone, diphenyl-(2, 4,6-trimethylbenzoyl)phosphine oxide, phenyl bis(2, 4,6trimethylbenzoyl)phosphine oxide, 2-hydroxy-2-methyl-1-phenyl-1-propanone, benzyl-dimethyl ketal, 2-methyl-1-[4-(methylthio)phenyl]-2-morpholinopropan-1-one, or combinations thereof. Non-limiting examples of additional photo initiators include alpha amino ketone UV photo initiators such as Ciba® Irgacure® 907, Ciba® Irgacure® 369, and Ciba® Irgacure® 379; bis acylphosphine oxide (BAPO) UV photo initiators such as Irgacure® 819, Darocur® 4265, and Darocur® TPO; alpha hydroxy ketone UV photo initiators such as Irgacure® 184 and Darocur® 1173; including photo initiators with or without sensitizers such as Darocur® ITX (2-isopropyl thioxanthone).

The colorant in the photo curable ink can be a pigment, a dye, or a combination thereof. In some examples, the colorant can be present in an amount from 0.5 wt % to 10 wt % in the photo curable ink. In one example, the colorant can be present in an amount from 1 wt % to 5 wt %. In another example, the colorant can be present in an amount from 5 wt % to 10 wt %.

In some examples, the colorant can be a dye. The dye can be nonionic, cationic, anionic, or a mixture of nonionic, cationic, and/or anionic dyes. Specific examples of dyes that can be used include, but are not limited to, Sulforhodamine B, Acid Blue 113, Acid Blue 29, Acid Red 4, Rose Bengal, Acid Yellow 17, Acid Yellow 29, Acid Yellow 42, Acridine Yellow G, Acid Yellow 23, Acid Blue 9, Nitro Blue Tetrazolium Chloride Monohydrate or Nitro BT, Rhodamine 6G, Rhodamine 123, Rhodamine B, Rhodamine B Isocyanate, Safranine O, Azure B, and Azure B Eosinate, which are available from Sigma-Aldrich Chemical Company (St. Louis, Mo.). Examples of anionic, water-soluble dyes include, but are not limited to, Direct Yellow 132, Direct Blue 199, Magenta 377 (available from Ilford AG, Switzerland), alone or together with Acid Red 52. Examples of water-insoluble dyes include azo, xanthene, methine, polymethine, and anthraquinone dyes. Specific examples of water-insoluble dyes include Orasol® Blue GN, Orasol® Pink, and Orasol® Yellow dyes available from Ciba-Geigy Corp. Black dyes may include, but are not limited to, Direct Black 154, Direct Black 168, Fast Black 2, Direct Black 171, Direct Black 19, Acid Black 1, Acid Black 191, Mobay Black SP, and Acid Black 2.

In other examples, the colorant can be a pigment. The pigment can be self-dispersed with a polymer, oligomer, or small molecule; or can be dispersed with a separate dispersant. Suitable pigments include, but are not limited to, the following pigments available from BASF: Paliogen® Orange, Heliogen® Blue L 6901F, Heliogen® Blue NBD 7010, Heliogen® Blue K 7090, Heliogen® Blue L 7101F, Paliogen® Blue L 6470, Heliogen® Green K 8683, and Heliogen® Green L 9140. The following black pigments are available from Cabot: Monarch® 1400, Monarch® 1300, Monarch® 1100, Monarch® 1000, Monarch® 900, Monarch® 880, Monarch® 800, and Monarch® 700. The following pigments are available from CIBA: Chromophtal® Yellow 3G, Chromophtal® Yellow GR, Chromophtal® Yellow 8G, Igrazin® Yellow 5GT, Igrantee Rubine 4BL, Monastral® Magenta, Monastral® Scarlet, Monastral® Violet R, Monastral® Red B, and Monastral® Violet Maroon B. The following pigments are available from Degussa: Printex® U, Printex® V, Printex® 140U, Printex® 140V, Color Black FW 200, Color Black FW 2, Color Black FW 2V, Color Black FW 1, Color Black FW 18, Color Black S 160, Color Black S 170, Special Black 6, Special Black 5, Special Black 4A, and Special Black 4. The following pigment is available from DuPont: Tipure® R-101. The following pigments are available from Heubach: Dalamar® Yellow YT-858-D and Heucophthal Blue G XBT-583D. The following pigments are available from Clariant: Permanent Yellow GR, Permanent Yellow G, Permanent Yellow DHG, Permanent Yellow NCG-71, Permanent Yellow GG, Hansa Yellow RA, Hansa Brilliant Yellow 5GX-02, Hansa Yellow-X, Novoperm® Yellow HR, Novoperm® Yellow FGL, Hansa Brilliant Yellow 10GX, Permanent Yellow G3R-01, Hostaperm® Yellow H4G, Hostaperm® Yellow H3G, Hostaperm® Orange GR, Hostaperm® Scarlet GO, and Permanent Rubine F6B. The following pigments are available from Mobay: Quindo® Magenta, Indofast® Brilliant Scarlet, Quindo® Red R6700, Quindo® Red R6713, and Indofast® Violet. The following pigments are available from Sun Chemical: L74-1357 Yellow, L75-1331 Yellow, and L75-2577 Yellow. The following pigments are available from Columbian: Raven® 7000, Raven® 5750, Raven® 5250, Raven® 5000, and Raven® 3500. The following pigment is available from Sun Chemical: LHD9303 Black. Any other pigment and/or dye can be used that is useful in modifying the color of the UV curable ink. Additionally, the colorant can include a white pigment such as titanium dioxide, or other inorganic pigments such as zinc oxide and iron oxide.

The components of the photo curable ink can be selected to give the ink good ink jetting performance. Besides the curable binder, polymeric amine synergists, photo initiator, and the colorant, the photo curable ink can also include a liquid vehicle. Liquid vehicle formulations that can be used in the photo curable ink can include water and one or more co-solvents present in total at from 1 wt % to 50 wt %, depending on the jetting architecture. Further, one or more non-ionic, cationic, and/or anionic surfactant can be present, ranging from 0.01 wt % to 20 wt % (if present). In one example, the surfactant can be present in an amount from 5 wt % to 20 wt %. The liquid vehicle can also include dispersants in an amount from 5 wt % to 20 wt %. The balance of the formulation can be purified water, or other vehicle components such as biocides, viscosity modifiers, materials for pH adjustment, sequestering agents, preservatives, and the like. In one example, the liquid vehicle can be more than 50 wt % water.

Classes of co-solvents that can be used can include organic co-solvents including aliphatic alcohols, aromatic alcohols, diols, glycol ethers, polyglycol ethers, caprolactams, formamides, acetamides, and long chain alcohols. Examples of such compounds include primary aliphatic alcohols, secondary aliphatic alcohols, 1,2-alcohols, 1,3-alcohols, 1,5-alcohols, ethylene glycol alkyl ethers, propylene glycol alkyl ethers, higher homologs ($C_6$-$C_{12}$) of polyethylene glycol alkyl ethers, N-alkyl caprolactams, unsubstituted caprolactams, both substituted and unsubstituted formamides, both substituted and unsubstituted acetamides, and the like. Specific examples of solvents that can be used include, but are not limited to, 2-pyrrolidinone, N-methylpyrrolidone, 2-hydroxyethyl-2-pyrrolidone, 2-methyl-1,3-propanediol, tetraethylene glycol, 1,6-hexanediol, 1,5-hexanediol and 1,5-pentanediol.

One or more surfactants can also be used, such as alkyl polyethylene oxides, alkyl phenyl polyethylene oxides, polyethylene oxide block copolymers, acetylenic polyethylene oxides, polyethylene oxide (di)esters, polyethylene oxide amines, protonated polyethylene oxide amines, protonated polyethylene oxide amides, dimethicone copolyols, substituted amine oxides, and the like. The amount of surfactant added to the formulation of this disclosure may range from 0.01 wt % to 20 wt %. Suitable surfactants can include, but are not limited to, liponic esters such as Tergitol™ 15-S-12, Tergitol™ 15-S-7 available from Dow Chemical Company, LEG-1 and LEG-7; Triton™ X-100, Triton™ X-405 available from Dow Chemical Company; LEG-1, and sodium dodecylsulfate.

Consistent with the formulation of this disclosure, various other additives can be employed to optimize the properties of the ink composition for specific applications. Examples of these additives are those added to inhibit the growth of harmful microorganisms. These additives may be biocides, fungicides, and other microbial agents, which are routinely used in ink formulations. Examples of suitable microbial agents include, but are not limited to, NUOSEPT® (Nudex, Inc.), UCARCIDE™ (Union carbide Corp.), VANCIDE® (R.T. Vanderbilt Co.), PROXEL® (ICI America), and combinations thereof.

Sequestering agents, such as EDTA (ethylene diamine tetra acetic acid), may be included to eliminate the deleterious effects of heavy metal impurities, and buffer solutions may be used to control the pH of the ink. From 0.01 wt % to 2 wt %, for example, can be used if present. Viscosity modifiers and buffers may also be present, as well as other additives to modify properties of the ink as desired. Such additives can be present at from 0.01 wt % to 20 wt % if present.

Table 1 shows the composition of an example of a photo curable ink, e.g., UV LED curable ink, formulation example in accordance with the present disclosure. The ink can be formulated by mixing these ingredients or by other formulations. The pH of the ink can then be adjusted. In one example, the ingredients can be stirred for 30 minutes, and then aqueous potassium hydroxide can be added to adjust the pH to 7 to 12, or in one example, about 8.5. It is noted that though water concentrations are listed as "balance," it is understood that the balance of components can include other liquid vehicle components or minor amounts of solids often present in inkjet ink compositions.

TABLE 1

| Component | Weight Percent |
| --- | --- |
| Photo reactive binder (UV reactive polymer) | 1-20% |
| Sensitizer | *0-10% |
| Co-photo initiator | *0-10% |
| Polymeric amine synergist | 0.15-10% |
| Surfactant | 0-20% |
| Anti-kogation agent | 0-5% |
| Colorant | 0.5-10% |
| Organic Co-solvent | 0.1-50% |
| Water | Balance |

*As noted, when a sensitizer is included, the amounts of sensitizer and co-photo initiator can be greater than 0%.

The photo curable ink can be used to print on a broad selection of substrates including untreated plastics, flexible as well as rigid, porous substrates such as paper, cardboard, foam board, textile, and others. The ink has a good adhesion on a variety of substrates. The photo curable ink also has a good viscosity, enabling good printing performances and enables the ability to formulate inks suitable for inkjet application. In some examples, the ink can be formulated for thermal inkjet printing. The photo curable ink composition of the present disclosure enables high printing speed and is very well suited for a use in digital inkjet printing.

The polymeric amine synergists of the present disclosure can be stable in aqueous environments at pH from 7 to 12 or higher. Thus, the photo curable ink can be formulated to have a pH from 7 to 12. In some examples, the photo curable ink can have a pH of 8 to 12. In one specific example, the photo curable ink can have a pH of about 8.5.

The polymeric amine synergists can exhibit less migration in cured ink compared with small molecule synergists. The photo curable binder in the ink can include polymers or monomers that polymerize or cross-link during the curing process. As the binder cures, the polymeric amine synergist can become locked into the cured binder due to the long polyether chain of the polymeric amine synergist. Therefore, the photo curable ink can be formulated so that there is little or no migration of the polymeric amine synergist in the ink after curing.

The present disclosure also extends to a method of making a photo curable ink. The method includes mixing a photo reactive binder; a photo initiator; optionally a co-photo initiator; a polymeric amine synergist; a colorant; and a liquid vehicle including co-solvent and water. The polymeric amine synergist can be an aminobenzene modified with a polyether chain connecting to the aminobenzene through an ether linkage. The photo curable ink can be UV curable, and in one specific example, UV LED curable. In one example, the method can also include adjusting the pH of the ink to be from 7 to 12. In another example, the method can include adjusting the pH of the ink to be 8 or higher.

It is to be understood that this disclosure is not limited to the particular process steps and materials disclosed herein because such process steps and materials may vary somewhat. It is also to be understood that the terminology used herein is used for the purpose of describing particular examples only. The terms are not intended to be limiting because the scope of the present disclosure is intended to be limited only by the appended claims and equivalents thereof.

It is noted that, as used in this specification and the appended claims, the singular forms "a," "an," and "the" include plural referents unless the context clearly dictates otherwise.

As used herein, "photoactive agent" refers to materials that participate in the initiation of photo polymerization, particularly materials that act as a photo initiator or a sensitizer for a photo initiator.

As used herein, "synergist" refers to a material that can be used with a type-II photo initiator to initiate polymerization of a curable binder.

As used herein, "UV curable" refers to compositions that can be cured by exposure to ultraviolet light from any UV source such as a mercury vapor lamp, UV LED source, or the like. Mercury vapor lamps emit high intensity light at wavelengths from 240 nm to 270 nm and 350 nm to 380 nm. "LED curable" refers to compositions that can be cured either by ultraviolet light from an ultraviolet LED. Ultraviolet LEDs emit light at specific wavelengths. For example, ultraviolet LEDs are available at 365 nm and 395 nm wavelengths, among others. The term "photo curable" refers generally to compositions that can be cured by exposure to light from any wavelength suitable for the composition being cured. Typically, the photo curable composition will be UV curable, and in some cases UV LED curable.

As used herein, "liquid vehicle" or "ink vehicle" refers to a liquid fluid in which colorant is placed to form an ink. A wide variety of ink vehicles may be used with the systems and methods of the present disclosure. Such ink vehicles may include a mixture of a variety of different agents, including, surfactants, solvents, co-solvents, anti-kogation agents, buffers, biocides, sequestering agents, viscosity modifiers, surface-active agents, water, etc.

As used herein, "colorant" can include dyes and/or pigments.

As used herein, "dye" refers to compounds or molecules that absorb electromagnetic radiation or certain wavelengths thereof. Dyes can impart a visible color to an ink if the dyes absorb wavelengths in the visible spectrum.

As used herein, "pigment" generally includes pigment colorants, magnetic particles, aluminas, silicas, and/or other ceramics, organo-metallics or other opaque particles, whether or not such particulates impart color. Thus, though the present description primarily exemplifies the use of pigment colorants, the term "pigment" can be used more generally to describe not only pigment colorants, but other pigments such as organometallics, ferrites, ceramics, etc. In one specific example, however, the pigment is a pigment colorant.

As used herein, "ink-jetting" or "jetting" refers to compositions that are ejected from jetting architecture, such as ink-jet architecture. Ink-jet architecture can include thermal or piezo architecture. Additionally, such architecture can print varying drop sizes such as less than 10 picoliters, less than 20 picoliters, less than 30 picoliters, less than 40 picoliters, less than 50 picoliters, etc.

The term "residual" when referring to remaining components after carrying out methods of the present disclosure can be up to 5 wt %, up to 3 wt %, up to 1 wt %, or up to 0.1 wt %, for example. To be clear, residual amounts of components are not necessarily present when reactants are fully consumed in a chemical reaction and such examples are included in the context of the present disclosure, but in practicality in many instances, some residual components can remain.

As used herein, the term "substantial" or "substantially" when used in reference to a quantity or amount of a material, or a specific characteristic thereof, refers to an amount that is sufficient to provide an effect that the material or characteristic was intended to provide. The exact degree of deviation allowable may in some cases depend on the specific context.

As used herein, the term "about" is used to provide flexibility to a numerical range endpoint by providing that a given value may be "a little above" or "a little below" the endpoint. The degree of flexibility of this term can be dictated by the particular variable and determined based on the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include individual numerical values or sub-ranges encompassed within that range as if each numerical value and sub-range is explicitly recited. As an illustration, a numerical range of "about 1 wt % to about 5 wt %" should be interpreted to include not only the explicitly recited values of about 1 wt % to about 5 wt %, but also include individual values and sub-ranges within the indicated range. Thus, included in this numerical range are individual values such as 2, 3.5, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

EXAMPLES

The following illustrates several examples of the present disclosure. However, it is to be understood that the following are only illustrative of the application of the principles of the present disclosure. Numerous modifications and alternative compositions, methods, and systems may be devised without departing from the spirit and scope of the present disclosure. The appended claims are intended to cover such modifications and arrangements.

Example 1

Synthesis of 4-dimethylaminophenol: To a solution of 4-aminophenol (54.65 g, 0.5 mol) in 600 mL of methanol was added formaldehyde (90 g, 3.0 mol) at room temperature. The above solution was cooled to −5° C. using a salted ice bath, and then sodium borohydride (113.5 g, 3.0 mol) was added portion wise. This reaction generated a significant amount of hydrogen gas, and therefore the sodium borohydride was added slowly for safety. After adding the sodium borohydride, the mixture was stirred at room temperature for 24 hours. The reaction was quenched via addition of ice-water and then extracted with chloroform (3×100 mL). The organic layer was combined and dried over sodium sulfate. Sodium sulfate was removed by filtration and the solvent was evaporated in vacuum. The residue was further purified by flash chromatography, giving the desired 4-dimethylaminophenol (56.3 g, 82% yield).

Example 2

Synthesis of dichloro-polyethylene glycol-600: A mixture of polyethylene glycol-600 (100 grams, 0.1 mol), thionyl chloride (60 grams, 0.5 mol) and 0.1 grams of N-dimethylformamide (DMF) was heated to reflux for 5 hours. After cooling down to room temperature, 20 mL of methanol was added slowly to the solution and stirred for 1 hour. Then the methanol and unreacted thionyl chloride were removed by vacuum to give the desired dichloro-polyethylene glycol (102 grams, 96% yield).

Example 3

Synthesis of polyethylene glycol di-tosylate: To a solution of polyethylene glycol-600 (100 grams, 0.167 mol) in 250 mL of dichloromethane was added pyridine (14 mL, 0.16 mol). The above solution was cooled to 0° C. and then p-toluenesulfonyl chloride (22.88 grams, 0.12 mol) was added portion-wise at 0° C. under $N_2$. The resulting solution was poured into ice-water. The organic layer was separated, and the aqueous layer was extracted with chloroform (2×50 mL). The combined organic layer was washed with water and dried over sodium sulfate. The sodium sulfate was filtered off and evaporation of solvent gave the desired polyethylene glycol di-tosylate (128 grams, 85% yield).

Example 4

Synthesis of chloro mono-methyl polyethylene glycol ether: A mixture of mono-methyl polyethylene glycol ether 550 (100 grams, 0.18 mol), thionyl chloride (60 grams, 0.5 mol) and 0.1 grams of N-dimethylformamide (DMF) was heated to reflux for 5 hours. After cooling down to room temperature, 20 mL of methanol was added slowly to the solution and stirred for 1 hour. Then the methanol and unreacted thionyl chloride were removed by vacuum to give the desired chloro mono-methyl polyethylene glycol ether (100 grams, 97% yield).

Example 5

Synthesis of mono-methyl polyethylene glycol ether tosylate: To a solution of mono-methyl polyethylene glycol ether 550 (100 grams, 0.182 mol) in 250 mL of dichloromethane was added pyridine (28 mL, 0.32 mol). The above solution was cooled to 0° C. and then p-toluenesulfonyl chloride (34.89 grams, 0.183 mol) was added portion-wise at 0° C. under $N_2$. The resulting solution was poured into ice-water. The organic layer was separated, and the aqueous layer was extracted with chloroform (2×50 mL). The combined organic layer was washed with water and dried over sodium sulfate. The sodium sulfate was filtered off and evaporation of solvent gave the desired mono-methyl polyethylene glycol tosylate (115 grams, 90% yield).

Example 6

Synthesis of bis(4-dimethylaminophenol) derivative of PEG 600 from dichloride: A mixture of 4-dimethylaminophenol (6.86 g, 50 mmol) and dichloro-polyethylene glycol-600 (15.88 g, 25 mmol) in 50 mL of DMF in the presence of sodium carbonate (5.3 g, 50 mmol) was heated to reflux for 3 hours. After cooling down to room temperature, the inorganic salts were removed by filtration. Evaporation of solvent by rotary evaporator gave a residue, which was further purified by flash chromatography, giving rise to the desired bis(4-dimethylaminophenol) derivative of PEG 600 (39.8 g, 95% yield).

Example 7

Synthesis of bis-(4-dimethylaminophenol) derivative of PEG 600 from di-tosylate: A mixture of 4-dimethylaminophenol (6.86 g, 50 mmol) and polyethylene glycol-600 di-tosylate (22.70 g, 25 mmol) in 50 mL of DMF in the presence of sodium carbonate (5.3 g, 50 mmol) was heated to reflux for 2 hours. Then DMF was removed by distillation. After cooling down to room temperature, the solid was filtered off by simple filtration. Evaporation of solvent by rotary evaporator gave a residue, which was further purified by flash chromatography, giving rise to the desired bis(4-dimethylaminophenol) derivative of PEG 600 (35.62 g, 85% yield).

Example 8

Synthesis of mono-(4-dimethylaminophenol) derivative of PEG 550 from chloride: A mixture of 4-dimethylaminophenol (6.86 g, 50 mmol) and chloro mono-methyl polyethylene glycol ether (28.38 g, 50 mmol) in 50 mL of DMF in the presence of sodium carbonate (5.3 g, 50 mmol) was heated to reflux for 2 hours. Then DMF was removed by distillation. After cooling down to room temperature, the solid was filtered off by simple filtration. Evaporation of solvent by rotary evaporator gave a residue, which was further purified by flash chromatography, giving rise to the desired mono-(4-dimethylaminophenol) derivative of PEG 550 (28.43 g, 85% yield).

Example 9

Synthesis of mono-(4-dimethylaminophenol) derivative of PEG 550 from tosylate: A mixture of 4-dimethylaminophenol (6.86 g, 50 mmol) and mono-methyl polyethylene glycol ether 550 tosylate (35.20 g, 50 mmol) in 50 mL of DMF in the presence of sodium carbonate (5.3 g, 50 mmol) was heated to reflux for 2 hours. Then DMF was removed by distillation. After cooling down to room temperature, the solid was filtered off by simple filtration. Evaporation of solvent by rotary evaporator gave a residue, which was further purified by flash chromatography, giving rise to the desired mono-(4-dimethylaminophenol) derivative of PEG 550 (30.1 g, 90% yield).

Example 10

Inkjet inks are prepared in accordance with the Table 1 above, each using one of polymeric amine synergists prepared in Examples 6-9. Specifically, inks are prepared that include the polymeric amine synergist; a photo reactive binder; a photo initiator; a colorant; and a liquid vehicle including co-solvent and water.

While the present technology has been described with reference to certain examples, those skilled in the art will appreciate that various modifications, changes, omissions, and substitutions can be made without departing from the spirit of the disclosure. It is intended, therefore, that the disclosure be limited only by the scope of the following claims.

What is claimed is:

1. A polymeric amine synergist composition, comprising a polymeric amine synergist including an aminobenzene modified with a polyether chain connecting to the aminobenzene through an ether linkage, wherein the polymeric amine synergist is present in a reaction product mixture with either i) an aminophenol, or ii) a carbonate base.

2. The polymeric amine synergist composition of claim 1, wherein the reaction product mixture comprises a carbonate base that is sodium carbonate, potassium carbonate, cesium carbonate, sodium bicarbonate, potassium bicarbonate, cesium bicarbonate, or a combination thereof.

3. The polymeric amine synergist composition of claim 2, wherein the carbonate base is present in an amount up to about 1.0 equivalent with respect to a total amount of aminophenol used to form the polymeric amine synergist.

4. A method of making a polymeric amine synergist, comprising reacting an aminophenol, a polyether modified with a leaving group, and a carbonate base in a single reaction step to yield a polymeric amine synergist that is an aminobenzene modified with a polyether chain connecting to the aminobenzene through an ether linkage.

5. The method of claim 4, wherein the carbonate base is sodium carbonate, potassium carbonate, cesium carbonate, sodium bicarbonate, potassium bicarbonate, cesium bicarbonate, or a combination thereof.

6. The method of claim 4, wherein the carbonate base is reacted in an amount from about 1.0 to about 2.0 equivalents with respect to a total amount of the aminophenol.

7. The method of claim 4, wherein the leaving group is chloride, bromide, iodide, tosylate, triflate, or a combination thereof.

8. The method of claim 4, wherein the aminophenol has the general formula:

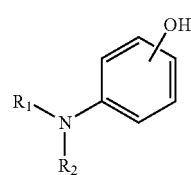

(I)

wherein $R_1$ and $R_2$ are independently a hydrogen atom, an unsubstituted alkyl, a substituted alkyl, an unsubstituted alkenyl, a substituted alkenyl, an unsubstituted aryl, a substituted aryl, an unsubstituted aralkyl, a substituted aralkyl, a halogen atom, —NO$_2$, —O—R$_d$, —CO—R$_d$, —CO—O—R$_d$, —O—CO—R$_d$, —CO—NR$_d$R$_e$, —NR$_d$R$_e$, —NR$_d$—CO—R$_e$, —NR$_d$—CO—O—R$_e$, —NR$_d$—CO—NR$_e$R$_f$, —SR$_d$, —SO—R$_d$, —SO$_2$—R$_d$, —SO$_2$—O—R$_d$, —SO$_2$NR$_d$R$_e$, or a perfluoroalkyl group, wherein R$_d$, R$_e$, and R$_f$ are independently a hydrogen atom, an unsubstituted alkyl, a substituted alkyl, an unsubstituted alkenyl, a substituted alkenyl, an unsubstituted aryl, a substituted aryl, an unsubstituted aralkyl, or a substituted aralkyl.

9. The method of claim 4, wherein the polyether modified with the leaving group is formed by reacting a leaving group with a polyether chain, wherein the polyether chain comprises polyethylene glycol, polypropylene glycol, or a copolymer of polyethylene glycol and polypropylene glycol.

10. The method of claim 9, wherein the polyether chain is PEG 550, PEG 600, or PEG 1000.

11. The method of claim 4, wherein the polyether modified with the leaving group has a general formula of:

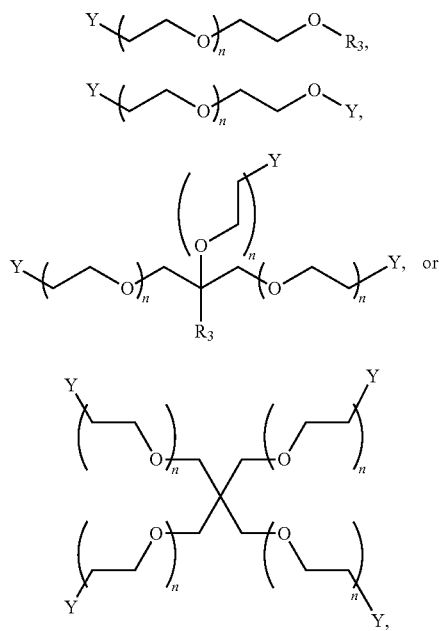

wherein R$_3$ is a hydrogen atom, an unsubstituted alkyl, a substituted alkyl, an unsubstituted alkenyl, a substituted alkenyl, an unsubstituted aryl, a substituted aryl, an unsubstituted aralkyl, a substituted aralkyl, a halogen atom, —NO$_2$, —O—R$_d$, —CO—R$_d$, —CO—O—R$_d$, —O—CO—R$_d$, —CO—NR$_d$R$_e$, —NR$_d$R$_e$, —NR$_d$—CO—R$_e$, —NR$_d$—CO—O—R$_e$, —NR$_d$—CO—NR$_e$R$_f$, —SR$_d$, —SO—R$_d$, —SO$_2$—R$_d$, —SO$_2$—O—R$_d$, —SO$_2$NR$_d$R$_e$, or a perfluoroalkyl group, wherein R$_d$, R$_e$, and R$_f$ are independently a hydrogen atom, an unsubstituted alkyl, a substituted alkyl, an unsubstituted alkenyl, a substituted alkenyl, an unsubstituted aryl, a substituted aryl, an unsubstituted aralkyl, or a substituted aralkyl, wherein Y is chloride, bromide, iodide, tosylate, or triflate, and wherein n is an integer from 5 to 200.

12. The method of claim 4, wherein the polymeric amine synergist has the formula:

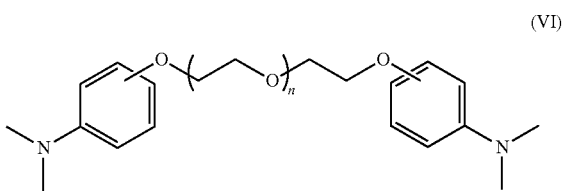

wherein n is an integer from 10 to 25.

13. The method of claim 4, wherein the polymeric amine synergist has a weight average molecular weight from about 500 Mw to about 5000 Mw, a water solubility of at least 0.5 wt %, is stable in water at a pH from 7 to 12, or combinations thereof.

14. A method of making a photo curable ink, comprising:
preparing a polymeric amine synergist in accordance with claim 4; and
admixing:
the polymeric amine synergist,
a photo reactive binder,
a photo initiator,
a colorant, and
a liquid vehicle including co-solvent and water.

15. A photo curable ink, comprising:
a polymeric amine synergist composition, comprising a polymeric amine synergist including an aminobenzene modified with a polyether chain connecting to the aminobenzene through an ether linkage;
an aminophenol, or a carbonate base, or combination thereof;
a photo reactive binder;
a photo initiator;
a colorant; and
a liquid vehicle including co-solvent and water.

* * * * *